(12) United States Patent
Payne et al.

(10) Patent No.: US 10,814,147 B2
(45) Date of Patent: Oct. 27, 2020

(54) THERAPEUTIC ULTRASOUND BREAST TREATMENT

(71) Applicant: University of Utah Research Foundation, Salt Lake City, UT (US)

(72) Inventors: Allison Payne, Salt Lake City, UT (US); Rock J. Hadley, Salt Lake City, UT (US); Robb P. Merrill, Salt Lake City, UT (US); Emilee Minalga, Salt Lake City, UT (US); Dennis L. Parker, Salt Lake City, UT (US); Laura Lighty, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 773 days.

(21) Appl. No.: 15/318,521

(22) PCT Filed: Jun. 15, 2015

(86) PCT No.: PCT/US2015/035838
§ 371 (c)(1),
(2) Date: Dec. 13, 2016

(87) PCT Pub. No.: WO2015/192134
PCT Pub. Date: Dec. 17, 2015

(65) Prior Publication Data
US 2017/0120078 A1    May 4, 2017

Related U.S. Application Data

(60) Provisional application No. 62/012,105, filed on Jun. 13, 2014.

(51) Int. Cl.
*A61N 7/00* (2006.01)
*A61N 7/02* (2006.01)
(Continued)

(52) U.S. Cl.
CPC ............... *A61N 7/00* (2013.01); *A61B 5/055* (2013.01); *A61B 5/4848* (2013.01);
(Continued)

(58) Field of Classification Search
CPC .... A61B 8/00; A61B 8/08; A61B 8/12; A61B 8/0825; A61B 8/406; A61B 5/0555;
(Continued)

(56) References Cited

U.S. PATENT DOCUMENTS 4,074,564 A   2/1978 Anderson
4,339,952 A   7/1982 Foster
(Continued)

OTHER PUBLICATIONS

Colas, Andre, and Jim Curtis. "Silicone biomaterials: history and chemistry." Biomaterials science: an introduction to materials in medicine 2 (2004): 80-5.*
(Continued)

*Primary Examiner* — Carolyn A Pehlke
(74) *Attorney, Agent, or Firm* — Thorpe North & Western, LLP

(57) ABSTRACT

A therapeutic ultrasound breast treatment device (101) is disclosed. The device (101) can include a receptacle (130) to receive a breast of a patient therein. The device (101) can also include an ultrasound transducer assembly disposed proximate the receptacle and oriented to direct a high intensity ultrasound transmission through an opening (168) of the receptacle (130) toward the breast. The device (101) can include a liner (1 60) disposed in the receptacle (130) to contain an ultrasound coupling fluid about the breast. The liner (160) can have an extension portion that extends through the opening (168) to form a seal with the ultrasound transducer assembly to prevent leakage of the ultrasound coupling fluid. A focus location of the ultrasound transmission can be adjustable and the device (101) can include a plurality of RF tracking coils to determine the focus location (Continued)

of the ultrasound transmission to facilitate adjustment of the focus location in an MRI environment.

20 Claims, 14 Drawing Sheets

(51) Int. Cl.
    *A61B 5/055*     (2006.01)
    *A61B 5/00*     (2006.01)
    *A61B 8/08*     (2006.01)
    *A61B 8/00*     (2006.01)
    *A61B 17/225*     (2006.01)
    *A61B 90/00*     (2016.01)

(52) U.S. Cl.
    CPC ............ *A61B 8/0825* (2013.01); *A61B 8/406* (2013.01); *A61N 7/02* (2013.01); *A61B 2017/2253* (2013.01); *A61B 2090/374* (2016.02); *A61N 2007/0091* (2013.01); *A61N 2007/0095* (2013.01)

(58) Field of Classification Search
    CPC ........ A61B 5/055; A61B 5/4848; A61N 7/00; A61N 7/02
    See application file for complete search history.

(56) References Cited

U.S. PATENT DOCUMENTS

| | | | |
|---|---|---|---|
| 4,545,385 A | 10/1985 | Pirschel | |
| 4,840,429 A | 6/1989 | Stockl | |
| 4,858,597 A | 8/1989 | Kurtze et al. | |
| 4,888,746 A | 12/1989 | Wurster et al. | |
| 5,020,855 A | 6/1991 | Lindberg et al. | |
| 5,186,162 A | 2/1993 | Talish et al. | |
| 5,522,869 A | 6/1996 | Burdette et al. | |
| 6,027,457 A | 2/2000 | Shmulewicz et al. | |
| 6,128,523 A | 10/2000 | Bechtold et al. | |
| 6,409,668 B1 * | 6/2002 | Wollschlaeger | A61B 8/0825 600/443 |
| 7,080,420 B2 | 7/2006 | Damron | |
| 7,134,157 B2 | 11/2006 | Koch | |
| 7,494,466 B2 | 2/2009 | Chauhan et al. | |
| 7,610,639 B2 | 11/2009 | Roleder et al. | |
| 7,611,196 B2 | 11/2009 | Terada et al. | |
| 7,699,783 B2 * | 4/2010 | Hanover | A61B 5/415 600/459 |
| 7,802,851 B2 | 9/2010 | Hyvarinen | |
| 7,871,130 B2 | 1/2011 | Da Silva Netto et al. | |
| 8,041,414 B2 | 10/2011 | Peter et al. | |
| 8,078,260 B2 | 12/2011 | Brasile | |
| 8,409,099 B2 | 4/2013 | Vitek et al. | |
| 2004/0082856 A1 | 4/2004 | Marmarelis | |
| 2005/0143638 A1 | 6/2005 | Johnson et al. | |
| 2006/0058678 A1 | 3/2006 | Vitek et al. | |
| 2006/0173307 A1 | 8/2006 | Amara et al. | |
| 2007/0250047 A1 | 10/2007 | Harter | |
| 2008/0167555 A1 | 7/2008 | Qian et al. | |
| 2009/0259122 A1 | 10/2009 | Larson et al. | |
| 2010/0056914 A1 | 3/2010 | Bruggers | |
| 2010/0069740 A1 | 3/2010 | Larson et al. | |
| 2011/0160566 A1 * | 6/2011 | Petropoulos | A61N 5/1049 600/411 |
| 2011/0237946 A1 | 9/2011 | Stribling | |
| 2011/0306870 A1 | 12/2011 | Kuhn | |
| 2012/0029358 A1 * | 2/2012 | Lin | A61B 8/0825 600/447 |
| 2013/0030283 A1 | 1/2013 | Vortman et al. | |
| 2013/0253322 A1 | 9/2013 | Suzuki et al. | |
| 2013/0304087 A1 | 11/2013 | Stuart | |
| 2016/0195594 A1 * | 7/2016 | Leussler | A61B 5/704 600/422 |

OTHER PUBLICATIONS

Extended European Search Report dated Feb. 2, 2018, in EP Application No. 15807575.4, filed Jun. 5, 2015, 7 pages.

Minalga et al, "An 11-Channel Radio Frequency Phased Array Coil for Magnetic Resonance Guided High-Intensity Focused Ultrasound of the Breast." Magnetic Resonance in Medicine; Wiley; Mar. 16, 2012; vol. 69, Issue 1; pp. 295-302.

Payne et al, "In Vivo Evaluation of a Breast-Specific Magnetic Resonance Guided Focused Ultrasound System in a Goat Udder Model." Med. Phys; Am. Assoc. Phys. Med.; Jul. 2013; vol. 40, Issue 7; pp. 073302-1-073302-9.

Payne et al, "Design and Characterization of a Laterally Mounted Phased-Array Transducer Breast-Specific MRgHIFU Device With Integrated 11-Channel Receiver Array." Med. Phys.; Am. Assoc. Phys. Med; Mar. 2012; vol. 39, Issue 3; pp. 1552-1560.

PCT Application No. PCT/2015/035838; Filing Date Jun. 15, 2015, Allison Payne, International Search Report, dated Nov. 12, 2015, 14 Pages.

* cited by examiner

THERAPEUTIC ULTRASOUND BREAST TREATMENT

RELATED APPLICATIONS

This application is a national stage entry of PCT International Application No. PCT/US2015/035838, filed Jun. 15, 2015 which claims the benefit of U.S. Provisional Application No. 62/012,105, filed Jun. 13, 2014, which is incorporated herein by reference.

GOVERNMENT INTEREST

This invention was made with government support under R01 CA134599 and R01 CA172787 awarded by the National Institutes of Health. The government has certain rights in the invention.

BACKGROUND

Breast cancer remains a devastating disease, adversely affecting a large population of women. Chances of developing breast cancer at some time in a woman's life are approximately 1 in 8. Despite more sensitive magnetic resonance imaging (MRI) methods to detect breast lesions and new minimally invasive conservative forms of therapy, there still remains significant room for improvement in both imaging and therapy. MRI-guided high-intensity focused ultrasound (MRgHIFU) has the potential to provide completely noninvasive therapy of localized breast cancer, avoiding the discomfort and potential complications associated with general anesthesia and surgery. MRgHIFU has the potential to improve cosmetic outcomes by avoiding scarring, and possibly allow earlier administration of systemic therapies due to shorter postoperative recovery time. Indeed, a minimally invasive treatment such as MRgHIFU may be the only viable treatment recourse when radiation or chemotherapy limits have been exhausted. A unique capability of MRI is the ability to monitor and assess thermal therapy treatments in near real-time. Most MRgHIFU breast treatments have utilized a vertically propagating transducer. A vertically propagating transducer can limit the areas that can be treated effectively with the device. In addition, with a vertically propagating transducer, the ultrasound can pass through the nipple or other undesired tissue, and can pass through the ribs or lungs and cause pain or other damage.

SUMMARY

A therapeutic ultrasound breast treatment device can include a receptacle to receive a breast of a patient therein. An ultrasound transducer assembly can be disposed proximate the receptacle and can be oriented to direct an ultrasound transmission through an opening of the receptacle toward the breast. A liner can also be disposed in the receptacle to contain an ultrasound coupling fluid about the breast. The liner can have an extension portion that extends through the opening to form a seal with the ultrasound transducer assembly to prevent leakage of the ultrasound coupling fluid.

In one aspect, a therapeutic ultrasound breast treatment device can include a receptacle to receive a breast of a patient therein. An ultrasound transducer assembly can be disposed proximate the receptacle and can be oriented to direct an ultrasound transmission into the receptacle toward the breast. More specifically, a focus location of the ultrasound transmission can be adjustable. When using magnetic resonance for imaging, a plurality of tracking coils can be oriented to determine the focus location of the ultrasound transmission to facilitate adjustment of the focus location.

In another aspect, a therapeutic ultrasound breast treatment device can include a receptacle to receive a breast of a patient therein. An ultrasound transducer assembly can be disposed adjacent the receptacle and can be oriented to direct an ultrasound transmission into the receptacle toward the breast. A radio frequency (RF) coil can be disposed within the receptacle proximate the breast to facilitate monitoring treatment of the breast using MRI.

In another aspect, a therapeutic ultrasound breast treatment device can include a receptacle to receive a breast of a patient therein and facilitate containment of an ultrasound coupling fluid about the breast. An ultrasound transducer assembly can be disposed proximate the receptacle and can be oriented to direct an ultrasound transmission into the receptacle toward the breast. A breast tensioning system can be included to counteract buoyancy of the breast and provide positional stability in the ultrasound coupling fluid. The breast tensioning system having a breast interface portion coupleable to the breast and a tensioning mechanism coupled to the breast interface portion to apply tension to the breast.

In another aspect, a therapeutic ultrasound breast treatment device can include a receptacle to receive a breast of a patient therein. An ultrasound transducer assembly can be disposed proximate the receptacle and oriented to direct an ultrasound transmission into the receptacle toward the breast through a transducer opening in the receptacle. A radio frequency coil can be disposed about the transducer opening to facilitate monitoring treatment of the breast using MRI.

In another aspect, a replaceable secondary RF coil module can include a locking base adapted to couple to a receptacle floor, a secondary RF coil, and at least one support member extending away from the locking base to orient the secondary RF coil a predetermined height and orientation above the locking base. The secondary RF coil can be inductively coupled to the primary RF coil (e.g. such as the one illustrated in FIG. 3).

In another aspect, a positioning device to movably adjust a position of a therapeutic ultrasound breast treatment device relative to a patient can include a base. A first mechanism can be coupled to the base. The first mechanism can be configured to provide straight line motion or quasi-straight line motion for at least a first portion of the first mechanism within a range of motion of the first mechanism in a first translational degree of freedom. A second mechanism can be coupled to the first portion of the first mechanism. The second mechanism can be configured to provide straight line motion or quasi-straight line motion for at least a second portion of the second mechanism within a range of motion of the second mechanism in a second translational degree of freedom. The second portion of the second mechanism can be positionable in the first translational degree of freedom by motion of the first mechanism. The second portion of the second mechanism can be positionable in the second translational degree of freedom by motion of the second mechanism.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
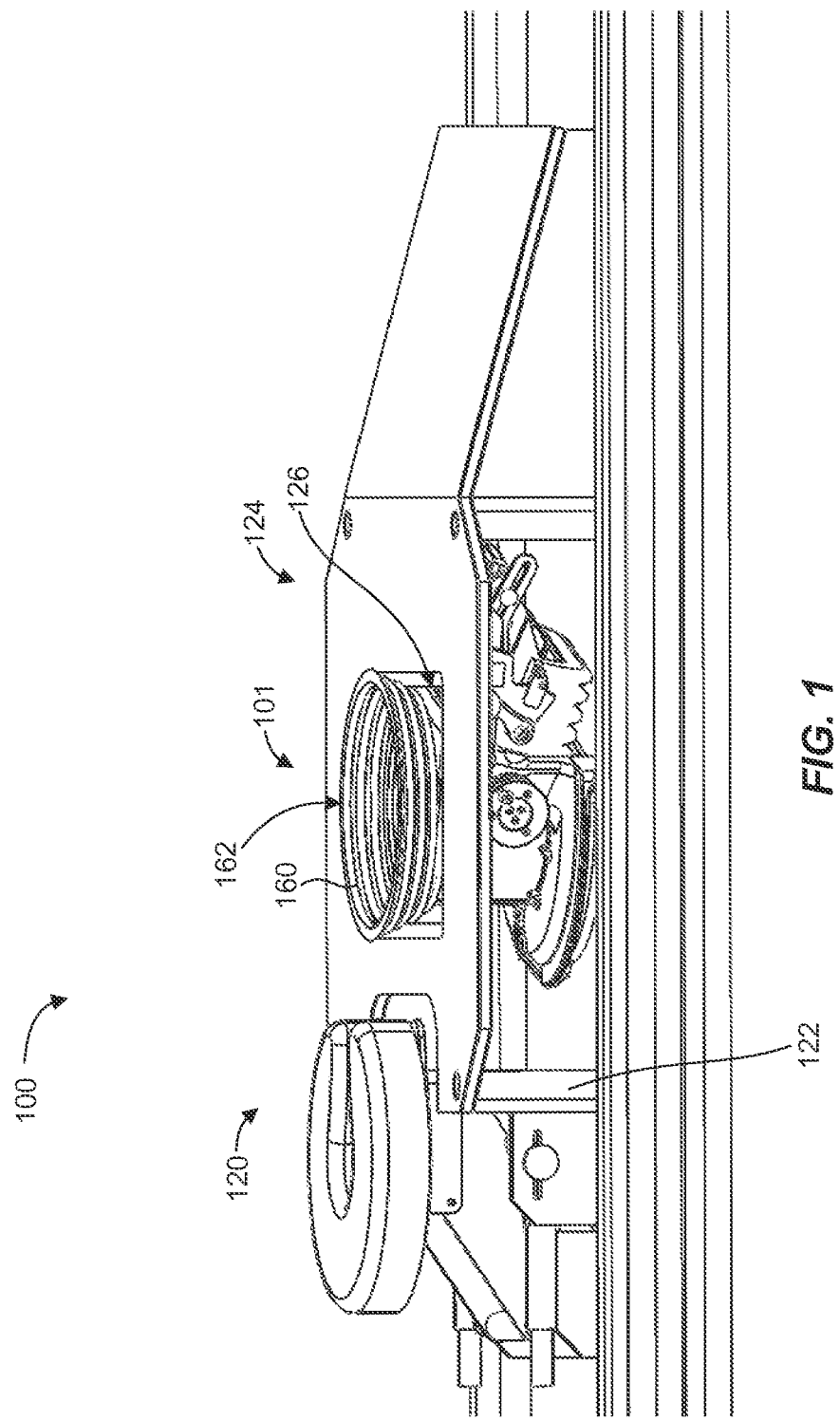
FIG. 1 illustrates a therapeutic ultrasound breast treatment system, in accordance with an example of the present disclosure.

These figures are provided merely for convenience in describing specific embodiments of the invention. Alteration in dimension, materials, and the like, including substitution, elimination, or addition of components can also be made consistent with the following description and associated claims. Reference will now be made to the exemplary embodiments illustrated, and specific language will be used herein to describe the same. It will nevertheless be understood that no limitation of the scope of the invention is thereby intended.

DETAILED DESCRIPTION

Reference will now be made to certain examples, and specific language will be used herein to describe the same. Examples discussed herein set forth therapeutic ultrasound breast treatment devices and systems that can effectively target the region of interest and provide improved MRI imaging compared to typical MRgHIFU devices. With the general embodiments set forth above, it is noted that when describing a therapeutic ultrasound breast treatment device, or the related methods, each of these descriptions are considered applicable to the other, whether or not they are explicitly discussed in the context of that embodiment. For example, in discussing the therapeutic ultrasound breast treatment device per se, the system and/or method embodiments are also included in such discussions, and vice versa.

It is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise.

Also, it is noted that various modifications and combinations can be derived from the present disclosure and illustrations, and as such, the following figures should not be considered limiting.

In describing and claiming the present invention, the following terminology will be used in accordance with the definitions set forth below.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Any steps recited in any method or process claims may be executed in any order and are not limited to the order presented in the claims unless otherwise stated. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Illustrated in FIG. 1 is a therapeutic ultrasound breast treatment system 100. The system 100 can include a therapeutic ultrasound breast treatment device 101 (shown isolated in FIG. 2). In one aspect, such a breast treatment device 101 can be an MRgHIFU device, which can be used for non-invasive surgical procedures, and typically includes one or more RF coils 110 for imaging, examples of which are shown isolated in FIG. 3 for clarity. Such a device creates focused spots of heat to destroy or alter tumors or other tissue within the body, as well as facilitates drug delivery, gene therapy, or the like. The system 100 can allow such procedures to be effectively applied to tissue within the breast, such as for cancer treatment. The system 100 can be used with multiple MRI field strengths. The system 100 can also include a patient support apparatus 120 that can have a base 122 and a patient interface portion 124 supported about the base 122 to position a breast of a patient for treatment by the therapeutic ultrasound breast treatment device 101, which can be disposed under at least a portion of the patient interface portion 124. In one aspect, the patient interface portion 124 can have an access opening 126 for passage of the breast into the treatment device 101. The patient support apparatus 120 can facilitate a prone position for the patient while being treated. Either breast can be treated individually. In one aspect, the patient support apparatus 120 can contain the ultrasound breast treatment device 101.

The therapeutic ultrasound breast treatment system 100 can be compatible with any suitable imaging system. Imaging systems can be used to image target tissue and treatment progress in real time or near real time (e.g. within several seconds). For example, the therapeutic ultrasound breast treatment system 100 can be adapted to use an MRI system to image target tissue. Further, the therapeutic ultrasound breast treatment system 100 can be configured to sit atop any size or patient table or configuration. All components of the system 100 can be designed to be MR compatible. For example, the ultrasound power generator can be designed to operate within an MRI scanner room and can be shielded to eliminate interactions with the MRI signals. The ultrasound control computer can be located outside the MRI scanner room and the control lines can penetrate the room. Alternatively, the imaging system can use x-ray radiography, ultrasonography, computed tomography, thermography, positron emission tomography, photoacoustic imaging, and the like.

Figure 2:
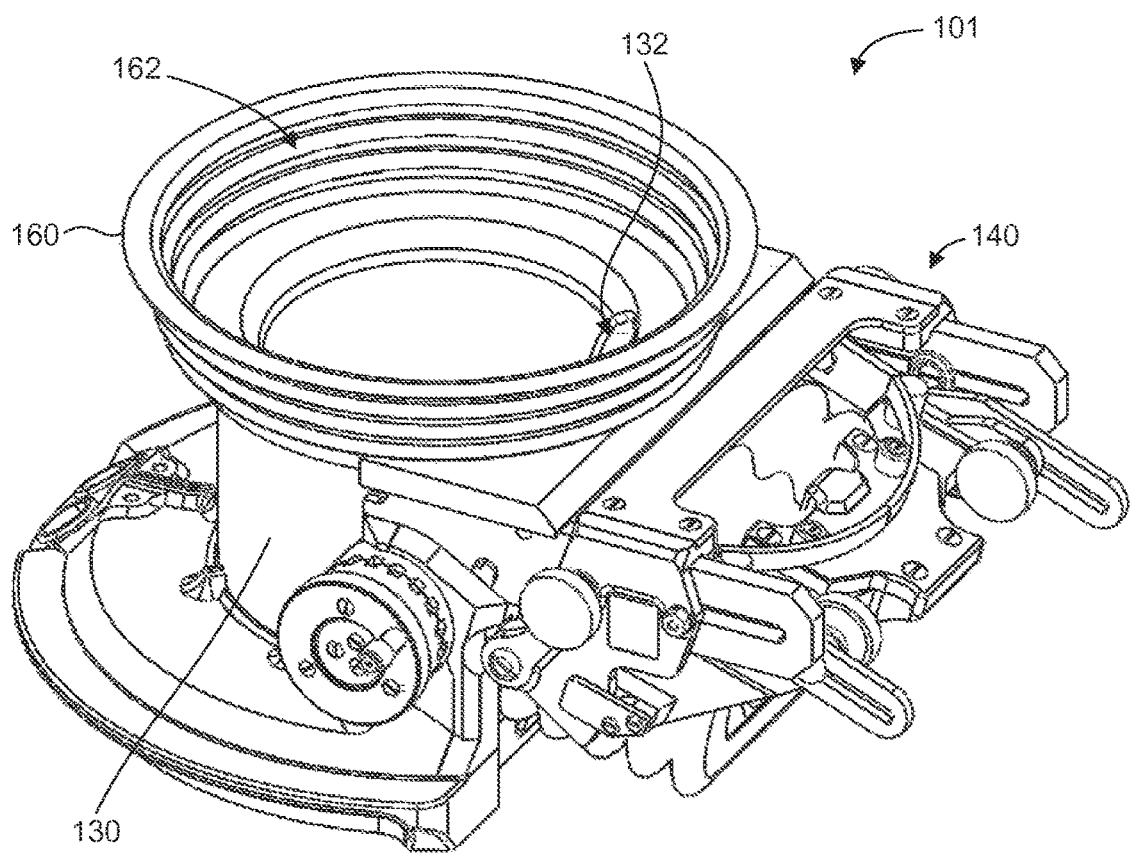
FIG. 2 illustrates a therapeutic ultrasound breast treatment device of the system of FIG. 1, in accordance with an example of the present disclosure.

With particular reference to FIG. 2, in general, the ultrasound breast treatment device 101 is configured such that the treated breast is suspended in a treatment receptacle 130, such as a cylinder made of plastic, configured to receive the breast. An ultrasound transducer assembly 140 disposed proximate the receptacle 130 is oriented to direct an ultrasound transmission into the receptacle 130 toward the breast through an acoustic window or opening 132 in the receptacle 130. A coupling fluid, such as water, can surround the breast to facilitate ultrasonic transmissions into the target tissue of the breast. Non-limiting examples of acoustic coupling fluids include degassed water, mineral oil, ultrasound gels, and the like. In one aspect, the treatment receptacle 130 can be disposed beneath the patient interface portion 124 on a positioning system (see FIGS. 15-20), which can allow the receptacle to be positioned under the patient to accommodate variations in patients' anatomy. For example, a positioning system can allow translation in X and Y directions relative to the patient and patient table. The positioning system can be moved manually or by using displacement motors which can move the treatment receptacle 130 and/or the device 101 to a predetermined position.

Figure 4A:
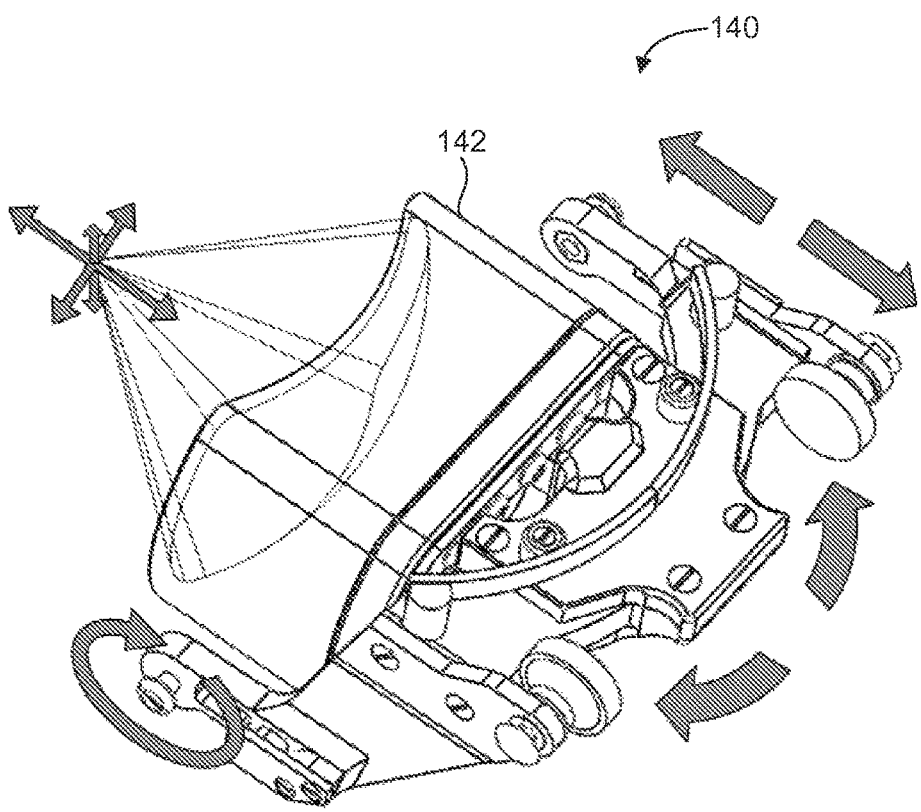
FIG. 4A illustrates mechanically moving a transducer assembly of the therapeutic ultrasound breast treatment device FIG. 2, in accordance with an example of the present disclosure.
Figure 4B:
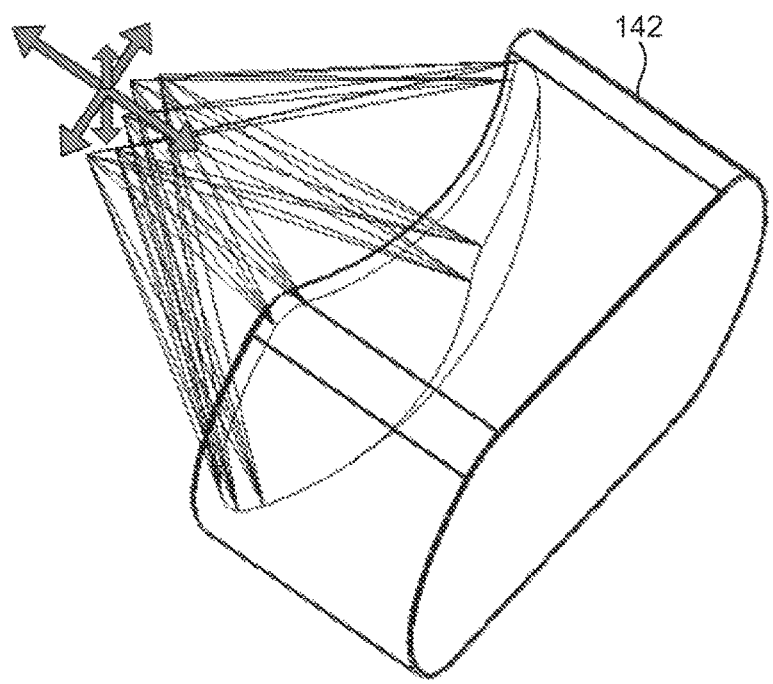
FIG. 4B illustrates electronically "steering" an ultrasound transmission from a transducer of the therapeutic ultrasound breast treatment device of FIG. 2, in accordance with an example of the present disclosure.

In one example, a phased-array ultrasound transducer 142 with adjustable focal point location positioning, via mechanically moving the ultrasound transducer 142 within the transducer assembly 140 (FIG. 4A) and/or electronic "steering" the ultrasound transmission from the ultrasound transducer 142 (FIG. 4B), can be mounted outside the treatment receptacle 130 to laterally direct or propagate ultrasound transmissions toward the breast in the receptacle 130. For example, as illustrated in FIG. 4A, the transducer 142 can be configured for rotation around its nominal axis, rotation in a plane perpendicular to the MR table around a nominal axis (e.g., oriented at 17 degrees with respect to horizontal), and/or translation toward and away from a central axis of the receptacle. In one alternative, both manual and electronic steering can be used to extend the treatment volume beyond focal point limits allowed by each option alone. In many cases, mechanical steering can be used for coarse adjustment to place a central focal point near a center of the target tissue. Subsequently, electronic steering can be used to make fine adjustments to focal point location and to ablate the target tissue within the electronic steering range (e.g. +/−15 mm in all directions). In one example, electronic steering can be accomplished by driving each element with independent magnitude and phase. Applying phase offsets to each element allows for steering the beam. Thus, mechanical positioning of the transducer 142 and electronic steering of the focal spot can enable placement of the ultrasound focus at desired locations throughout the suspended breast. The ultrasound breast treatment device 101 can be configured to treat all or a majority of a breast volume. Although FIG. 4A illustrates a mechanical adjustment which moves the transducer 142 relative to the receptacle 130, the entire receptacle assembly can alternatively be moved relative to target tissue. The transducer 142 can be any transducer which can deliver ultrasonic energy. Non-limiting examples of ultrasound transducers can include conventional transducers and focused transducers which are capable of HIFU such as those available from Imasonics SAS (e.g. 200 KHz-10 MHz frequency range, shaping capability, etc.), or the like.

Figure 3:
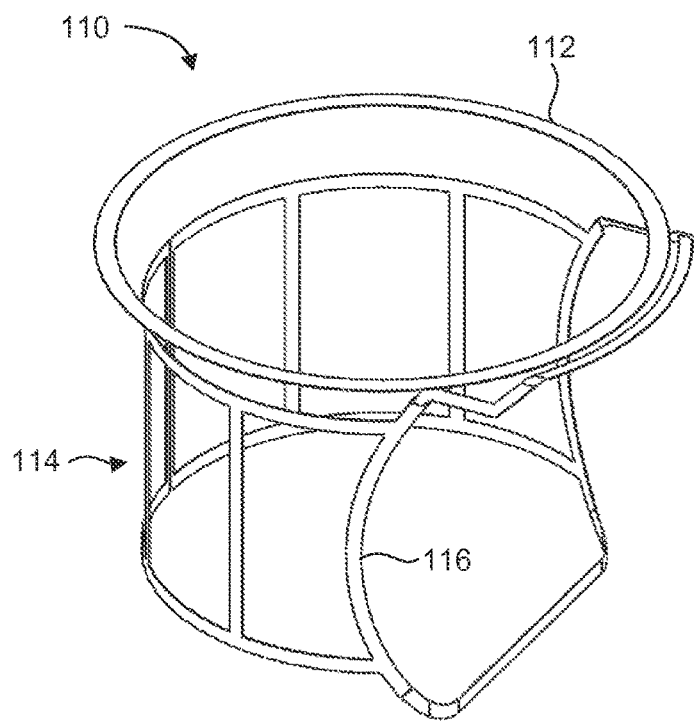
FIG. 3 illustrates RF coils of the therapeutic ultrasound breast treatment device of the system of FIG. 2, in accordance with an example of the present disclosure.

The array of RF coils 110 shown in FIG. 3 can be located around the breast and surrounding the transducer 142 to facilitate monitoring treatment of the breast using MRI. In one aspect, a single loop RF coil 112 can be located around the breast at the chest wall. In another aspect, one or more RF coils 114 can surround the outer surface of the receptacle 130, which can improve image quality over use of only a single loop coil at the chest wall. The RF coil 114 disposed about an exterior of the receptacle 130 can optionally comprise a phased array RF coil. In one optional aspect, the RF coil 140 can be arranged as a ladder-type or ladder array configuration wrapped from one edge of the treatment receptacle 130 window (e.g., transducer opening) around the receptacle 130 to the opposite edge of the window. In another more specific alternative, the RF coil 114 can include elements which extend into the treatment window. Such elements can be sufficiently thin to avoid distortion of the ultrasound beam, while also increasing a signal to noise ratio near a location of ultrasound entrance into the skin. In one aspect, the phased array could have any number of loops around the receptacle 130 and those loops can be in any orientation with respect to one another around the treatment receptacle 130. In another aspect, a RF coil 116 can be disposed about the transducer opening in the treatment cylinder, which can increase the signal-to-noise ratio (SNR) in the near field of the transducer 142. This can improve efficiency by allowing for the clear visualization of the transducer face and can increase safety by improving patient tissue temperature monitoring in all breast tissue.

In one aspect, the ladder array coil 114 can include loops at the top and/or bottom, with the top and/or bottom loop being adjustable in size (e.g. manufactured based on desired performance). The loops of the exterior coil configuration can be reduced in size to minimize sensitivity to the coupling fluid, which can minimize RF coil loading effects and reduce background noise in the MRI images. As the coil loops are minimized in size their signal sensitivity penetration depth into the breast is also reduced, which can decrease the signal of interest in the MRI images. For maximum signal sensitivity of the exterior coil array, or for maximum coil performance, and for maximum image quality of the MRI image, this phased array configuration can be positioned with the RF coils 114 as close to the breast as the outer surface of the receptacle 130 will allow, to maximize signal sensitivity potential from the breast. In order to create images with the greatest SNR in the volume of the breast, the individual loops of the phased array coil can be sized and positioned so that coil noise from the coupling fluid and breast tissue is minimized, the signal sensitivity in the breast is maximized and the inductive coupling between the individual loops is minimized. For each coil in the array, the coil loop size can be determined independent of other coils in the array and independent from the single RF coil 112 at the chest wall. However, the loop position is dependent upon the positions of the other loops and can result in minimum magnetic coupling to adjacent loops. Each RF coil element utilized, such as coils in the phased array receptacle coil 114, the single loop chest coil 112, and the coil 116 about the transducer opening, work together as a composite phased array coil to provide optimal SNR throughout the volume of the breast. Loop sizes other than the optimal sizes may be used for any loop in the phased array at the expense of decreased signal sensitivity in the breast volume. Similarly, the number of loops can be increased or decreased.

In one aspect, reducing or minimizing the diameter of the receptacle 130 can bring the ladder array RF coil closer to the breast volume-of-interest (VOI), therefore increasing the SNR in the breast tissue. In another aspect, reducing or minimizing the height of the receptacle 130 can reduce the volume of water in the receptacle 130, which can reduce the noise level seen by the breast during the treatment thus increasing SNR in the breast region of interest ROI.

All electronics can be protected by water-proofing and isolated from the outside environment to provide better mechanical stability to the electronics of the RF coils. In one aspect, preamps and printed circuit boards can be located at or near a lower portion of the receptacle 130, which can facilitate positioning the chest wall of the patient closer to the top of the receptacle 130 and therefore closer to the RF coils for improved patient positioning and reduced copper shielding of the MRI gradients. In one aspect, the breast can be lowered further in to the ladder coils 114 increasing the overall SNR in the breast ROI.

Figure 5:
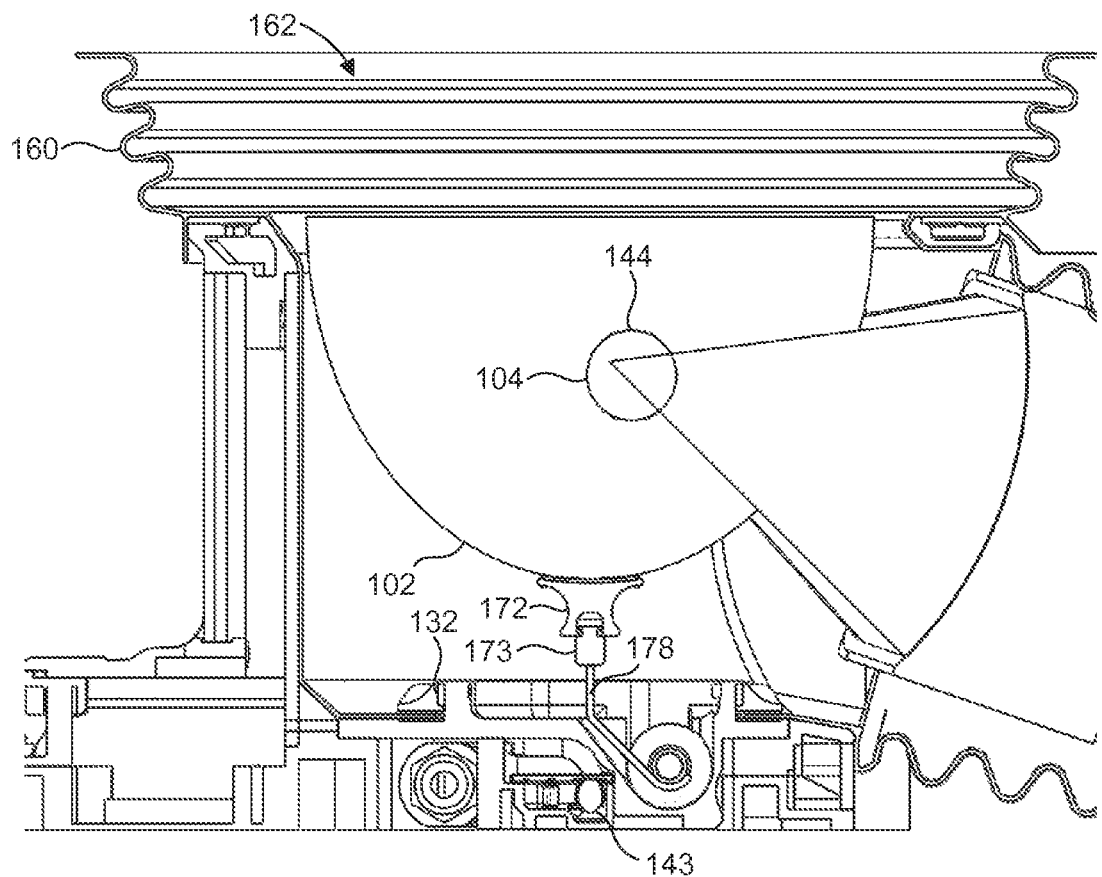
FIG. 5 illustrates a cross-sectional view of the therapeutic ultrasound breast treatment device of FIG. 2 in relationship to a breast undergoing treatment.

As discussed above, the transducer assembly 140 can be moved in multiple degrees of freedom (FIG. 4A) for moving the ultrasound focal point while performing a procedure on the patient. In addition, the receptacle 130 and the transducer assembly 140 can be configured for rotation around the treated breast, as illustrated in FIG. 5. In general, the therapeutic ultrasound breast treatment system 100 can be configured to facilitate a low position of the breast in the receptacle 130 to provide more effective treatment coverage volume. In addition, the effective treatment coverage volume can be improved by providing transducer assembly 140 adjustability as close as possible to the chest wall of the patient. An overflow tank (not shown) can be provided to contain any coupling fluid that is displaced by the motion of the transducer 142.

Mechanical manipulation of the transducer 142 position can be performed manually and/or via motorized means. Registration marks, electronic encoders and/or metrics can be located on the receptacle 130 and/or patient platform to facilitate repeatable placement of the transducer 142 and/or the receptacle 130, such as when used in conjunction with MRI scans of the breast and/or the tracking coils described below.

Figure 6:
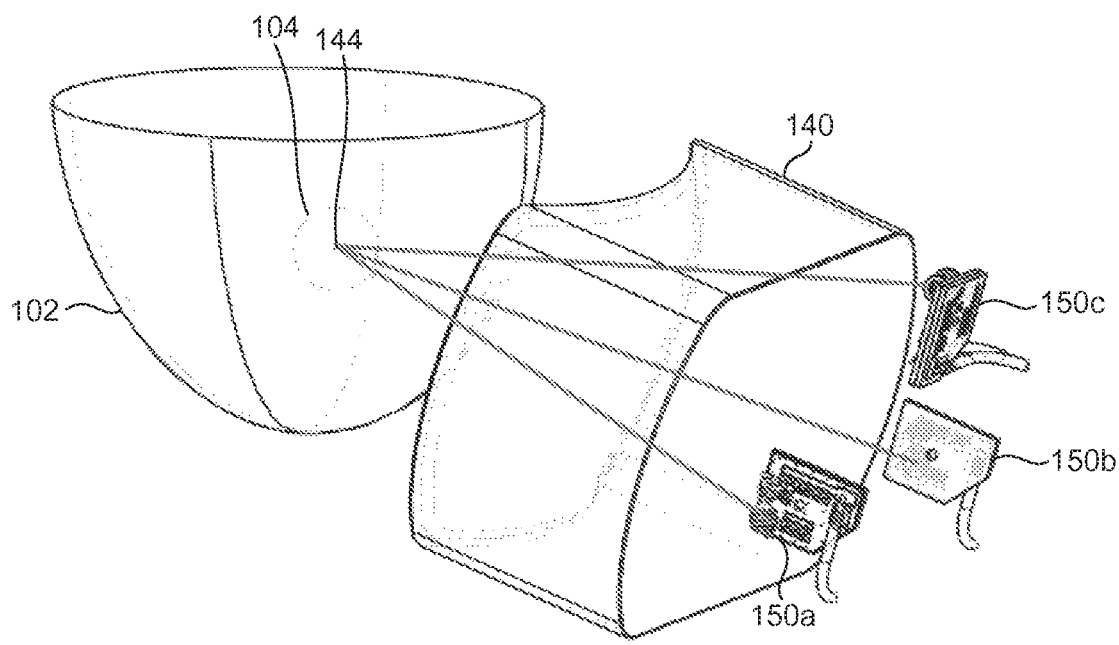
FIG. 6 illustrates tracking coils that can be included with the ultrasound breast treatment device of FIG. 2, in accordance with an example of the present disclosure.

FIG. 6 illustrates tracking coils 150a-c as part of an electromagnetic tracking system that can be included with an ultrasound breast treatment device in accordance with the present disclosure to determine the focus location 144 of the ultrasound transmission from the transducer 142 to facilitate adjustment of the focus location. For example, the tracking coils 150a-c can be configured to accurately indicate the position and orientation of the ultrasound transducer 142 relative to the breast 102 in the MRI coordinates, thus accurately locating the ultrasound beam focus 144 in the MR images and allowing accurate targeting of the ultrasound beam and registration of the patient without depositing focused ultrasound energy in the patient. The tracking coils 150a-c can optionally be each wrapped around a small bead and the high RF signal from the bead can be detected when a RF excitation pulse and magnetic gradient is applied. The decoded received signal gives precise localization of the bead in MR coordinates. By assessing the signal from each coil, the position and orientation of the transducer can be determined. Thus, the positions and orientations of the tracking coils 150a-c can be detected when moving within the coordinate space. The tracking coils 150a-c can be associated with the transducer 142 and/or the receptacle 130.

In one aspect, the tracking coils 150*a-c* can be used to determine the location of the ultrasound focus 144 for proper transducer adjustment, without making manual measurements based on MR images. In another aspect, the tracking coils 150*a-c* can be "automated" mathematically, such that the focal point location 144 can be calculated from tracking coil coordinates and provided in a usable frame of reference. For safety, the ultrasound transducer 142 can be activated for treatment only when the transducer 142 is properly adjusted to target a tumor 104. Additionally, tracking coils 143 can optionally be placed on or adjacent to the receptacle 130.

Figure 7:
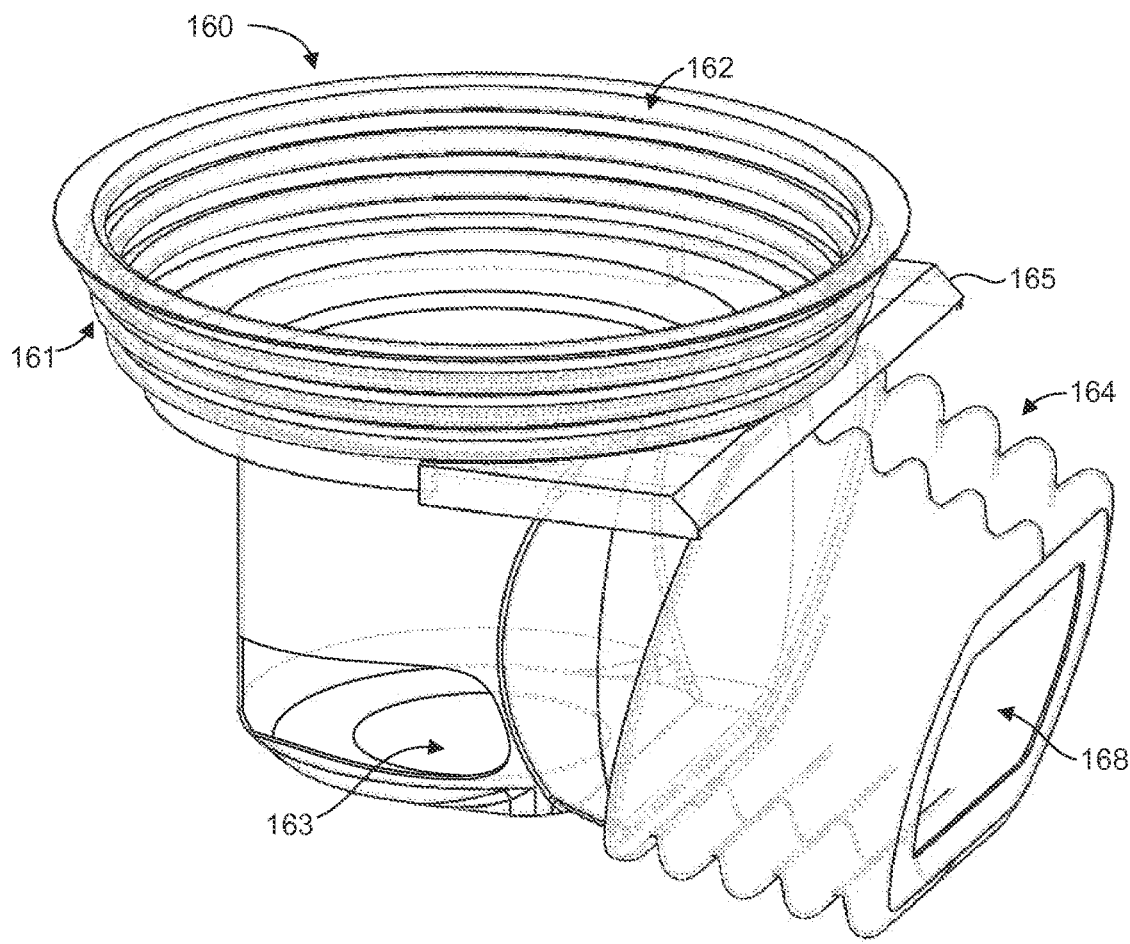
FIG. 7 illustrates a liner of the therapeutic ultrasound breast treatment device of FIG. 2.

In one aspect, the ultrasound breast treatment device 101 can include a liner 160 disposed in the receptacle 130 to contain the ultrasound coupling fluid about the breast 102. The liner 160 is shown isolated in FIG. 7 and in cross-section with a portion of the device 101 in FIG. 8. The liner 160 can be constructed of a flexible material which provides a fluid barrier or waterproof material, such as but not limited to silicone, nitrile, and the like. The liner 160 can have an opening 162 to receive the breast 102. The liner 160 can also have an extension portion 164, which can include a flexible bellows portion 166 with a transducer opening 168 that extends through the acoustic window or opening 132 of the receptacle 130 to form a seal with the ultrasound transducer assembly 140 to prevent leakage of the ultrasound coupling fluid. In one aspect, the ultrasound breast treatment device 101 can include a flexible bellows, which is not part of a liner, coupled to the transducer assembly 140 to facilitate movement of the transducer assembly 140 relative to the receptacle 130. In addition to the transducer opening 168, the liner 160 can include an opening 163 at the base to provide interior access for any suitable device component, such as a secondary RF coil as discussed below. The transducer opening 168 and the base opening 163 can be secured in place by retention rings to fluidly seal the openings and secure the liner. The liner 160 can have a flexible top 161 to conform to the patient's anatomy around the breast. The liner 160 can be configured to minimize the coupling fluid volume needed, which can reduce image artifacts that occur due to certain coupling fluids such as those often used by HIFU systems. With a reduced water volume and small receptacle diameter, the RF coil array 110 can be positioned close to the breast, enabling much higher signal to noise ratio than other devices. In one aspect, the liner 160 can include a drip cover 165 to protect or shield sensitive electronic components.

The liner 160 can be optically transparent sufficient to visually inspect the breast and acoustic coupling fluid through the liner to ensure proper placement of the breast within the receptacle 130. The liner 160 can be constructed with a mold having a polished surface finish to provide a smooth outer surface, thus enabling visibility through the liner.

In one aspect, the liner 160 can be replaceable and provided in a range of sizes to accommodate different breast sizes that will fit within the device 101. Although the liner 160 may be used over several treatments, in another aspect, the liner 160 can be disposed and replaced after each use. The liner 160 can facilitate a better coupling to the chest wall, thus increasing the acoustic window of the breast, and provide separation of the acoustic coupling fluid and system components (i.e. the transducer and/or a tensioning system, discussed below) thereby simplifying the disinfectant steps necessary between patients.

Figure 8:
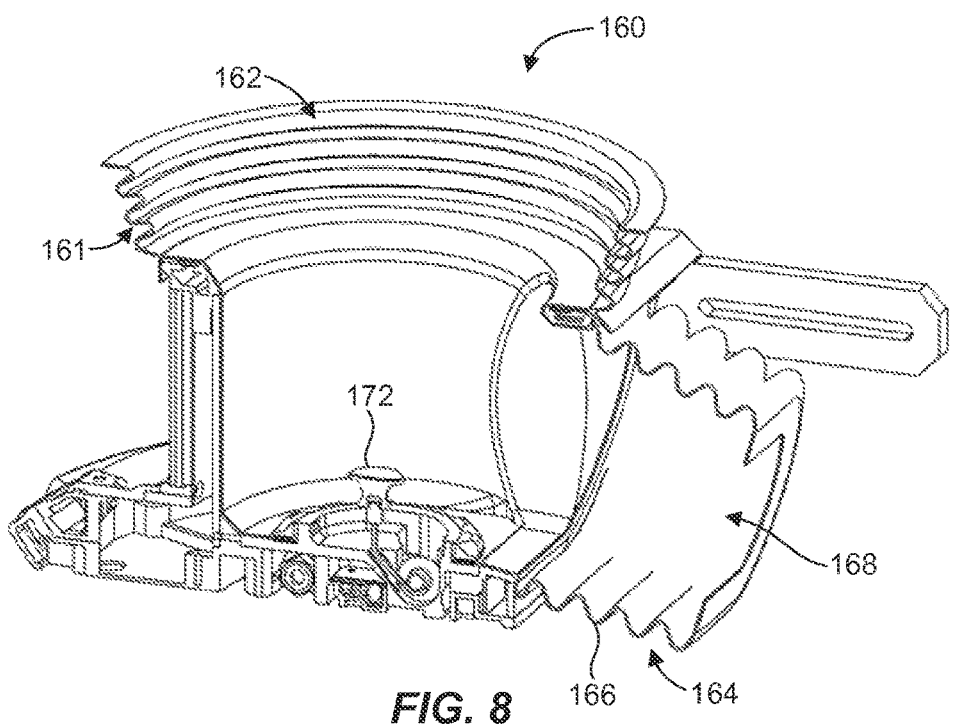
FIG. 8 illustrates a cross-sectional view of the therapeutic ultrasound breast treatment device of FIG. 2.
Figure 9:
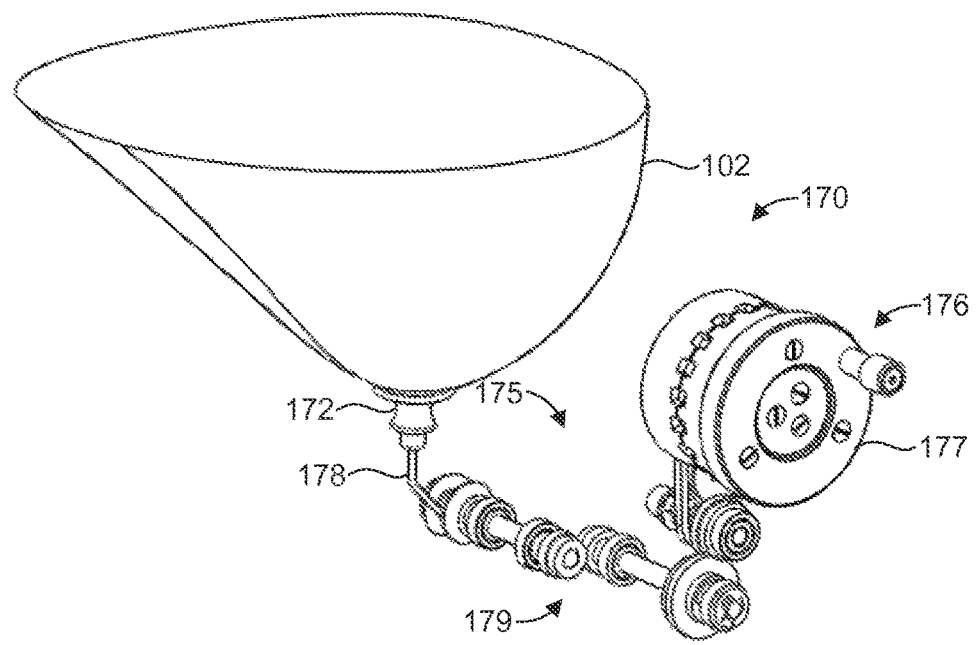
FIG. 9 illustrates a breast tensioning system that can be included with the ultrasound breast treatment device of FIG. 2, in accordance with an example of the present disclosure.

FIG. 9 illustrates a breast tensioning system 170 that can be included with an ultrasound breast treatment device in accordance with the present disclosure, portions of which are also shown in FIGS. 5 and 8. At least a portion of the breast tensioning system 170 can be incorporated within the receptacle 130 to elongate and reduce motion of the breast for repeatable positioning from treatment to treatment and to counteract buoyancy effects that occur when the breast is suspended in the acoustic coupling fluid inside the receptacle 130 (i.e. fatty breast tissue tends to have high buoyancy). As a result, additional tissue can be retained within accessible treatment volumes.

Figure 11A:
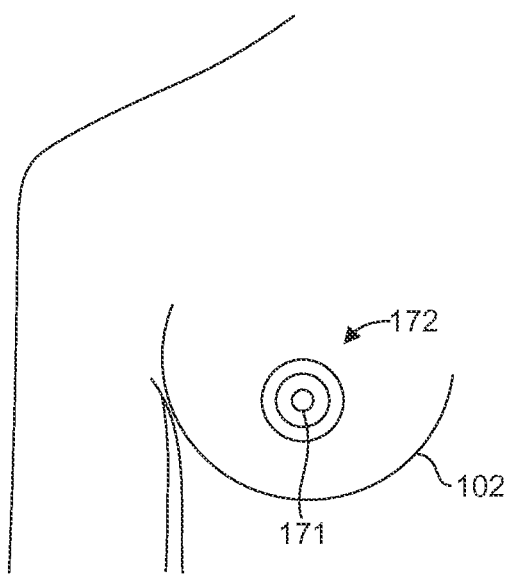
FIGS. 11A and 11B illustrate a breast interface portion of the breast tensioning system of FIG. 9 secured to a breast, in accordance with an example of the present disclosure.
Figure 11B:
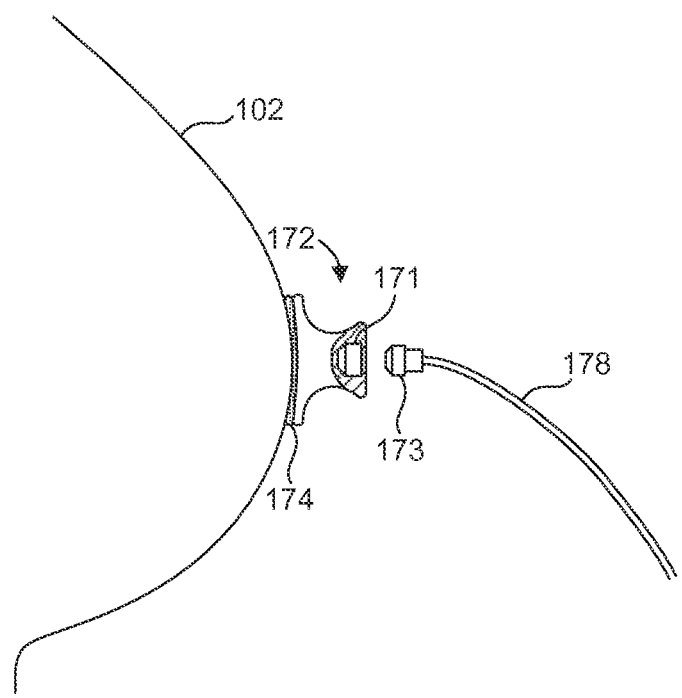
Figure 12A:
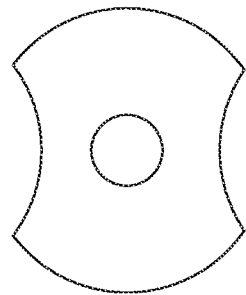
FIGS. 12A-12D illustrate of breast interface portion configurations, in accordance with several examples of the present disclosure.
Figure 12B:
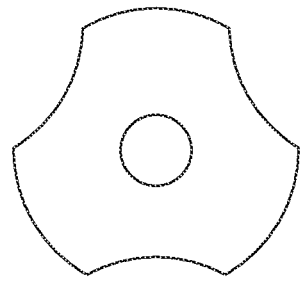
Figure 12C:
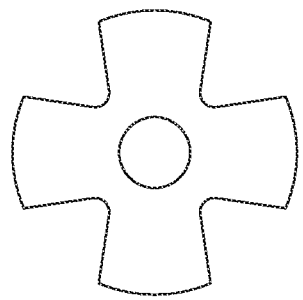
Figure 12D:
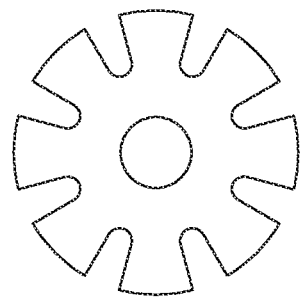

In one aspect, the breast tensioning system 170 can include a breast interface portion 172 (see, in particular, FIGS. 11A and 11B) coupleable to the breast 102, such as over a nipple of the treated breast and secured in any suitable manner, such as with an adhesive (e.g., a double-sided adhesive strip 174 or silicone tape), vacuum suction, etc. The breast interface portion 172 can be configured to be at least semi-flexible and semi-acoustically transparent (e.g., a molded silicone construction). The breast interface portion 172 can be of any suitable shape or configuration (see FIGS. 12A-12D). In one aspect, the breast interface portion 172 can comprise an adhesive and can, in a particular aspect, be an adhesive strip.

In another aspect (see, in particular, FIG. 9), the breast tensioning system 170 can include a tensioning device 176 coupled to the breast interface portion 172 to apply tension to the breast 102. Mild tension can be applied to the breast 102 by the tensioning device 176 after the patient is positioned on the device 101. The tensioning device 176 can include a tension line 178 (e.g., a cord, cable, etc.) and a force application mechanism 175. In one aspect, the force application mechanism 175 can include a force input device 177 and a transmission 179. In this case, the force input device 177 comprises a hand crank (i.e., unpowered or human-powered) that is configured to apply tension to the tension line 178 via the transmission 179, which is illustrated as a gear train. The tension line 178 can be configured to wind and unwind around a spool coupled to the transmission 179. In one aspect, the breast tensioning system can 170 be compatible with the liner 160 by extending the tension line 178 through the base opening 163 of the liner 160, which can separate the mechanics of the tensioning system 170 from the acoustic coupling fluid. It should be recognized that any suitable force input device 177 can be utilized (e.g., a weight) and can comprise any suitable human interface to provide force or torque and/or a mechanical, electrical, and/or electromechanical device (e.g., a motor) to provide force or torque. It should also be recognized that any suitable mechanism or device can be utilized as a transmission 179, such as a belt, pulley, chain, linkage mechanism, etc., to transfer force or torque to the breast interface portion 172. In the figures, force is transferred to the breast interface portion 172 from the force input device 177 via the gear train transmission 179 and the tension line 178. The breast interface portion 172 can include a coupling feature 171 configured to mate with a coupling feature 173 at an end of the tension line 178. Any suitable coupling feature can be utilized. The design of the breast interface portion 172 can allow technician to attach the tension line 178 to the breast interface portion 172 after the breast interface portion 172 has been attached to the breast 102 (e.g., by the patient).

Figure 10:
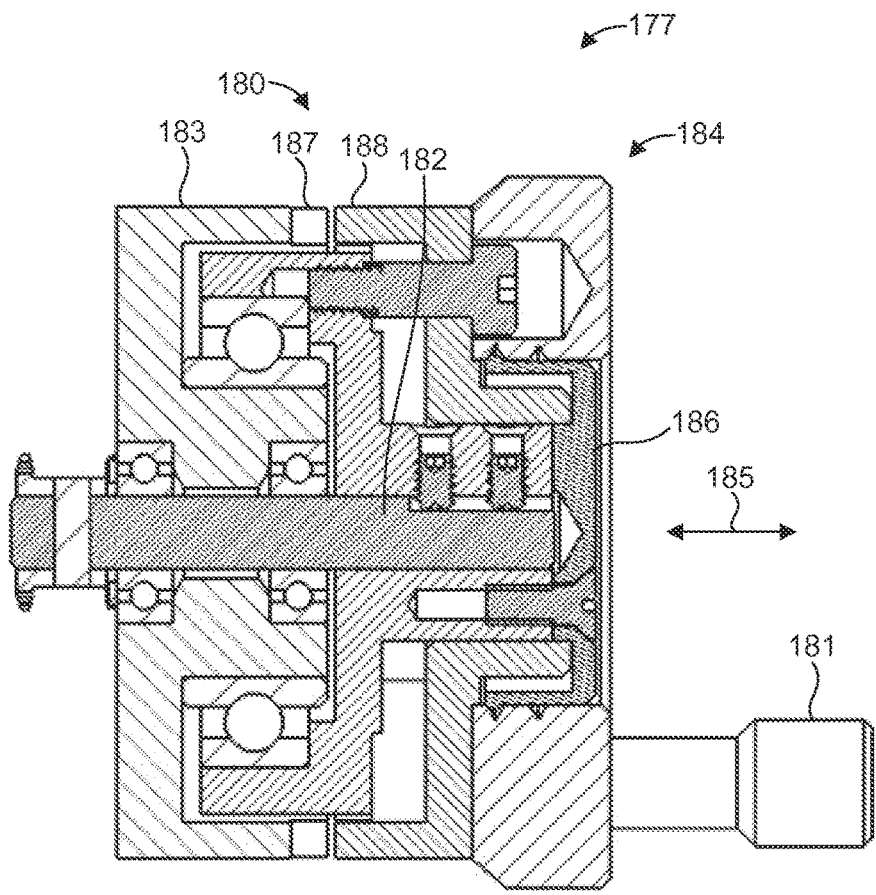
FIG. 10 illustrates a cross-sectional view of a hand crank of the breast tensioning system of FIG. 9, in accordance with an example of the present disclosure.

In one aspect, the tensioning device 176 can be configured to hold or maintain tension on the breast 102. For example, the force input device 177, such as a hand crank, can include a locking mechanism 180 configured to alternately facilitate rotation of the hand crank (e.g., to apply or release tension on the breast) or fixing a rotational position of the hand crank (e.g., to maintain tension on the breast 102). As shown in FIG. 10, the hand crank 177 can include a handle 181 configured to rotate a shaft 182. The shaft 182 can be supported by and rotatable relative to a fixed support portion 183. The handle 181 can be coupled to a rotating portion 184, which can be configured to cause rotation of the shaft 182. The locking mechanism 180 is configured such that the rotating portion 184 can move in direction 185 parallel to an axis of rotation of the shaft to alternately engage and disengage the fixed support portion 183, thereby alternately fixing a rotational position of the shaft 182 or facilitating rotation of the shaft. In one aspect, the engagement of the rotating portion 184 and the fixed support portion 183 can create a mechanical interference formed by mating engagement teeth 187, 188. Thus, the locking mechanism 180 can provide for graduated or indexed locking of the shaft 182 at various rotational positions thereby allowing the tension on the breast 102 to be precisely controlled and maintained during operation of the ultrasound breast treatment device. A center portion 186 of the rotating portion 184 can remain fixed in the direction 185 such that an operator can operate the hand crank 177 and locking mechanism 180 with a single hand by utilizing a thumb to push on the center portion 186 to disengage the engagement teeth 187, 188. Alternately the locking mechanism 180 can include a brake or a clutch to secure and release the rotating portion 184 relative to the fixed support portion 183.

Figure 13:
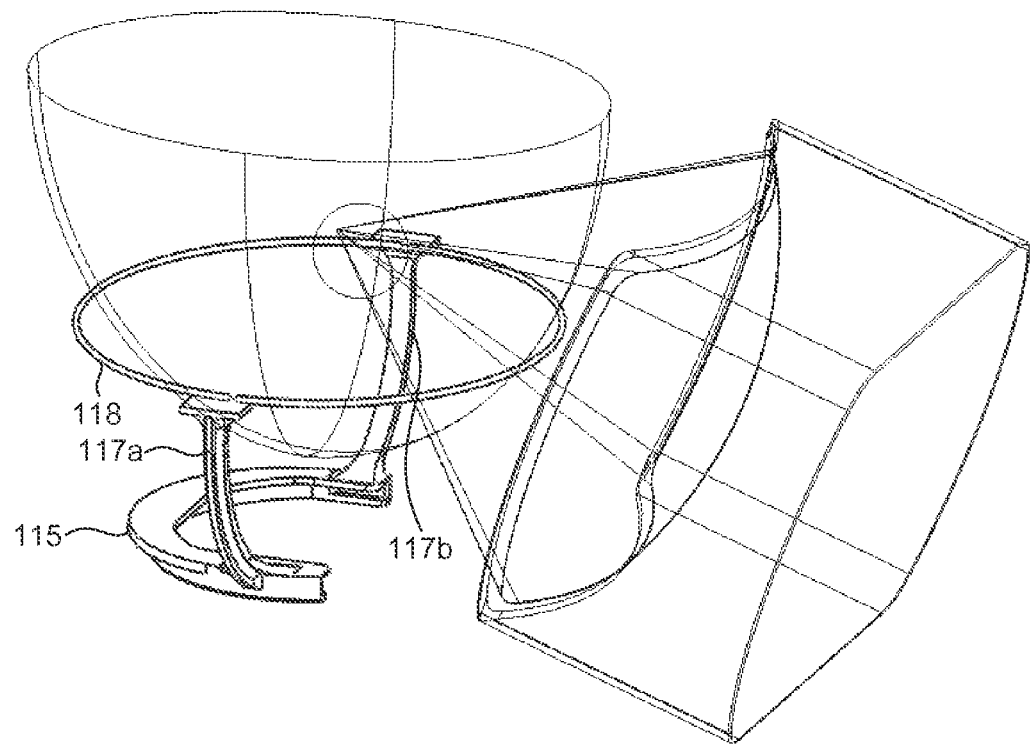
FIG. 13 illustrates a secondary RF coil that can be included with the ultrasound breast treatment device of FIG. 2, in accordance with an example of the present disclosure.
Figure 14:
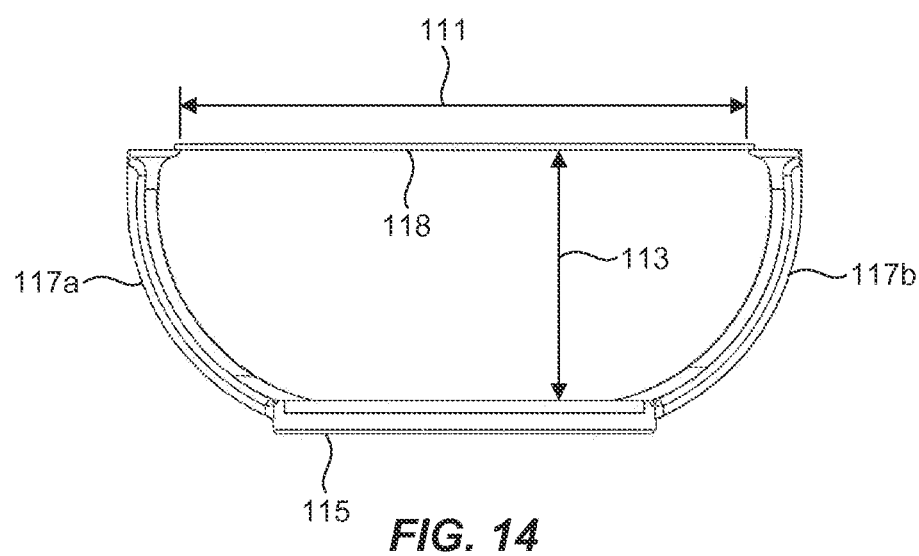
FIG. 14 illustrates a side view of the secondary RF coil of FIG. 13.

FIG. 13 illustrates a secondary or supplementary RF coil 118 that can be included with an ultrasound breast treatment device in accordance with the present disclosure to facilitate MRI monitoring treatment of the breast. The secondary RF coil 118 can be disposed within the receptacle 130 proximate the breast 102 and can further increase image detail through the center of the breast without affecting the ultrasonic transmission. The secondary RF coil 118 can be an inductively coupled loop that allows for obtaining SNR in a region closer to the breast ROI without interfering with the ultrasound beam by increasing the SNR in the region of interest. The secondary coil 118 can be removable and provided with different size rings to accommodate different sized breasts by varying diameter 111 and height 113 dimensions (FIG. 14). For example, the secondary coil 118 can include a locking base 115 which interfaces with a base retention coupling 134 in a floor of the receptacle 130 (see FIG. 5). One or more extension members 117a, 117b can elevate the RF coil 118 (e.g. a ring) a desired height above the locking base 115. Thus, the RF coil 118 can be electrically coupled to the device 101 via the locking base 115 to transmit signals to augment imaging. Multiple coil elements also allow for parallel imaging reconstruction which can facilitate increased imaging rates.

Figure 15:
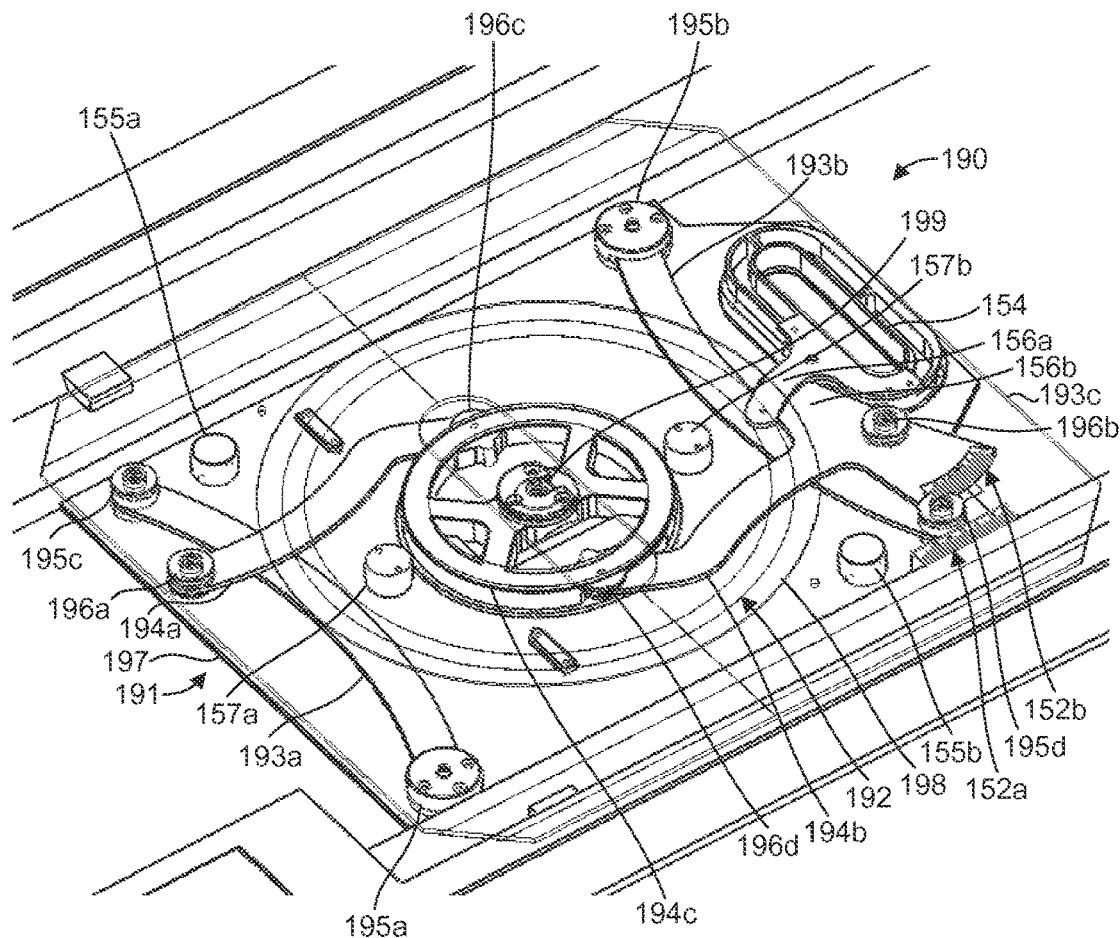
FIG. 15 illustrates a positioning device that can be included in a therapeutic ultrasound breast treatment system to movably adjust a position of an ultrasound breast treatment device, in accordance with an example of the present disclosure.
Figure 16:
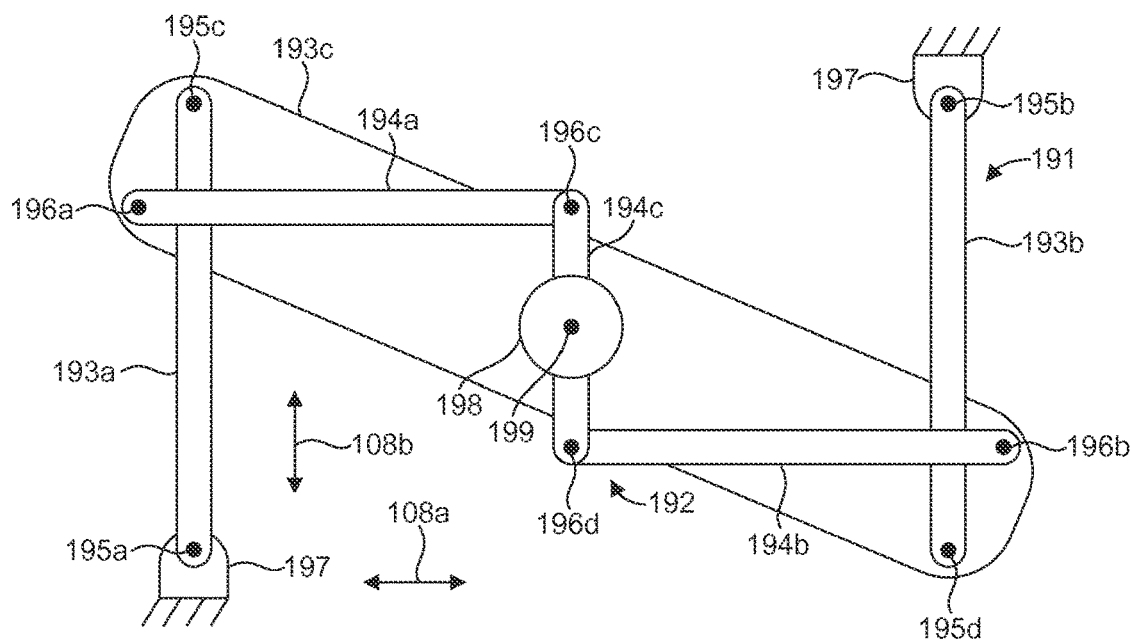
FIG. 16 illustrates a schematic representation of the positioning device of FIG. 15.

FIG. 15 illustrates a positioning device 190 that can be included in the therapeutic ultrasound breast treatment system 100 to movably adjust a position of the ultrasound breast treatment device 101 relative to a patient, in accordance with an example of the present disclosure. The positioning device 190 can include a base 197, a first mechanism 191 coupled to the base, and a second mechanism 192 (192 and 198 in FIG. 15 are parts of the protractor gauge for pivot 199, similar to 398 in FIG. 20) coupled to the first mechanism. A simplified schematic representation or diagram of the mechanisms 191, 192 of the positioning device 190 is shown in FIG. 16. The positioning device 190 can be constructed of any suitable material. The positioning device 190 illustrated in FIG. 15 is made substantially of a transparent material, such as polycarbonate sheet, which enables visibility of many of the components of the device 190.

The first mechanism 191 can include linkage members 193a-c and the second mechanism 192 can include linkage members 194a-c. The first mechanism 191 is coupled to the base 197, via the linkage member 193a at a pivot point 195a and via the linkage member 193b at a pivot point 195b. The linkage member 193c is coupled to the linkage member 193a at pivot point 195c and to the linkage member 193b at pivot point 195d. The second mechanism 192 is coupled to the linkage member 193c of the first mechanism 191 via the linkage member 194a at a pivot point 196a and via the linkage member 194b at a pivot point 196b. The linkage member 194c is coupled to the linkage member 194a at pivot point 196c and to the linkage member 194b at pivot point 196d.

The first mechanism 191 and/or the second mechanism 192 can be configured to provide straight line motion or quasi-straight line motion. Such motion can be for at least a portion of the mechanism within a range of motion of the mechanism in a translational degree of freedom. For example, at least a portion of the linkage member 193c of the first mechanism 191 is configured to move in straight line motion or quasi-straight line motion within a predefined range of motion in a translational degree of freedom 108a. Similarly, at least a portion of the linkage member 194c of the second mechanism 192 is configured to move in straight line motion or quasi-straight line motion within a predefined range of motion in a translational degree of freedom 108b. Thus, a portion of the linkage member 194c of the second mechanism 192 is positionable in the translational degree of freedom 108a by motion of the first mechanism 191 and in the translational degree of freedom 108b by motion of the second mechanism 192. In other words, the first and second mechanisms 191, 192 are independently movable in different translational degrees of freedom to position a portion of the linkage member 194c of the second mechanism 192 at a desired location, which can be related to Cartesian coordinates. Limit features 155a-b, 157a-b can serve as range of motion limit stops for the first mechanism 191 in degree of freedom 108a and for the second mechanism 192 in degree of freedom 108b, respectively. Lengths of linkage members 193a-b, 194a-b can be maximized in order to minimize rotation of the linkage members 193c, 194c, respectively, to better approximate straight line motion.

Any portion of the first or second mechanism 191, 192 can be configured to move in straight line motion or quasi-straight line motion, such as a middle portion of a linkage member and/or a portion of a linkage member proximate a pivot point. The first mechanism and/or the second mechanism can comprise a Watt linkage, a Peaucellier-Lipkin linkage, Hart linkage, a Chebyshev linkage, a Hoekens linkage, a Sarrus linkage, and/or a Scott Russell linkage, or any other linkage mechanism that can provide straight line motion or quasi-straight line motion. The first and second mechanisms illustrated in FIGS. 15 and 16 are Watt linkages.

Quasi-straight line motion is any motion that is sufficiently straight over the desired range of motion to serve as an adequate approximation of straight line motion. Variations from straight line motion evident in quasi-straight line motion can be accounted for by gaps or spacings between adjacent moving components. Thus, a mechanism providing quasi-straight line motion for a desired range of motion in a translational degree of freedom of the positioning system 190 can be close enough to true straight line motion that the positioning system will function adequately as intended.

In addition, a rotatable member 198 can be rotatably coupled to a portion of the second mechanism 192, such as via the linkage member 194c at a pivot point 199, to provide a rotational degree of freedom. Thus, the ultrasound breast treatment device 101 can be coupled to the rotatable member 198, which can provide movement of the device 101 in two translational degrees of freedom and a rotational degree of freedom about a vertical axis, for adjustability of the device 101 beneath a patient.

In one aspect, reference markings can be included and calibrated to indicate distance traveled in a given degree of freedom. For example, a reference or scale 152a can be associated with the linkage member 193c and the base 197 to indicate movement or position in the translational degree of freedom 108a, and a reference or scale 152b can be associated with the linkage member 194b and the linkage member 193c to indicate movement or position in the translational degree of freedom 108b. In addition, rotational position can be reference by relative movement of the rotatable member 198 and the linkage member 193c by placing angular graduations on a rotational gauge 198 which are measured against a straight line indicator mark on 193c parallel to degree of freedom 108b. Such references or indicators can be used to provide accurate and repeatable position adjustments when used in conjunction with MRI scans of the breast and the system tracking coils. The positioning device 190 can be configured with a low profile to provide measureable translation and rotation of the device 101 in a limited space.

A handle 154 can be included to facilitate portability of the positioning device 190. An extension arm 156a can provide a fixed location for securing to a portion 156b of the linkage member 194b to prevent movement of the first and second mechanisms 191, 192 during transport.

Figure 17:
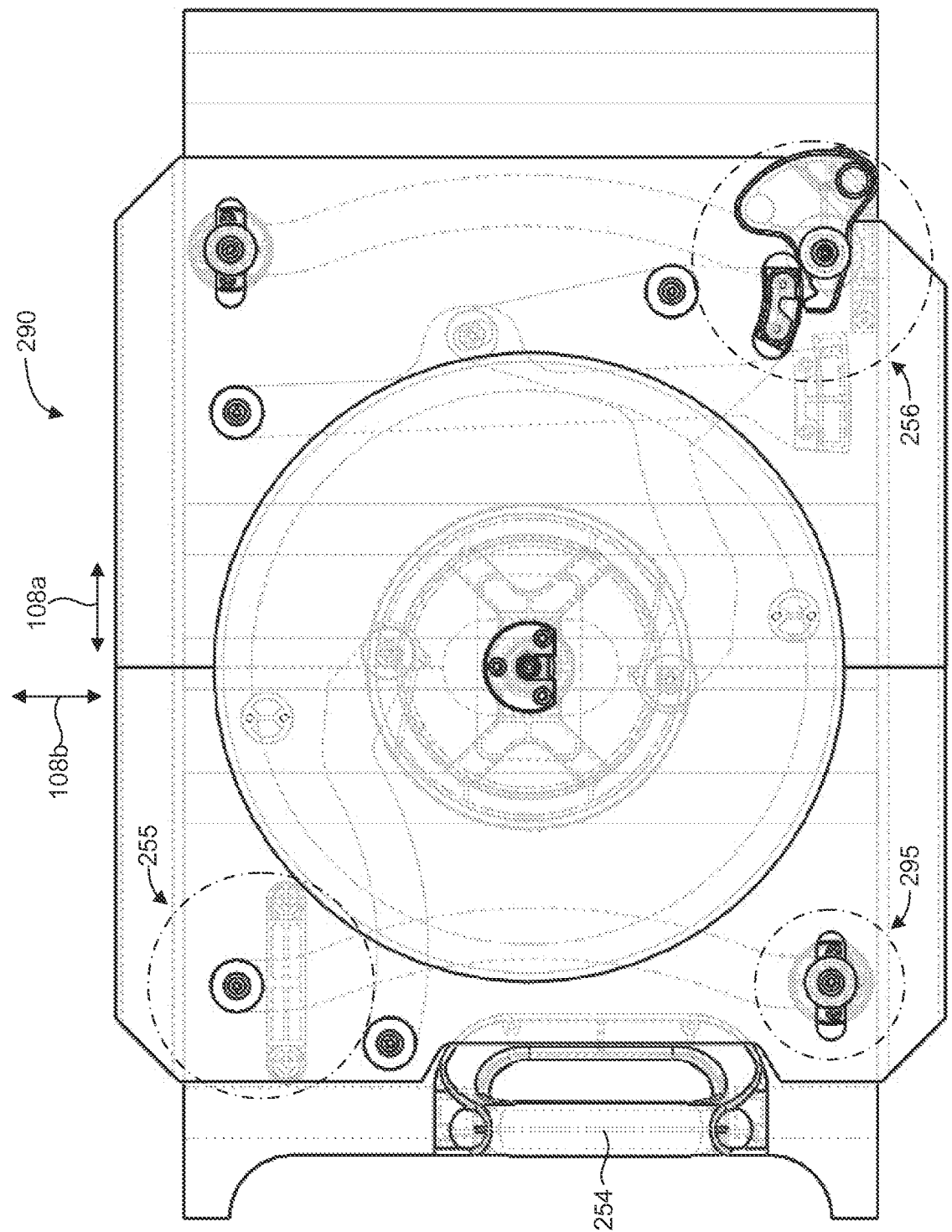
FIG. 17 illustrates a positioning device that can be included in a therapeutic ultrasound breast treatment system to movably adjust a position of an ultrasound breast treatment device, in accordance with another example of the present disclosure.

FIG. 17 illustrates a positioning device 290 that can be included in the therapeutic ultrasound breast treatment system 100 to movably adjust a position the ultrasound breast treatment device 101 relative to a patient, in accordance with another example of the present disclosure. The positioning device 290 is similar to the positioning device 190 in many respects, particularly with regard to having mechanisms configured to provide straight line motion or quasi-straight line motion, and these aspects will not be addressed in detail with respect to the positioning device 290. FIG. 17 illustrates several features that are absent or differ from those found in the positioning device 190 of FIG. 15, and which are shown in detail in FIGS. 18A-19C. For convenience, reference to features and components of the positioning device 290 will utilize similar reference numbers as used to refer to the features and components of the positioning device 190.

Figure 18A:
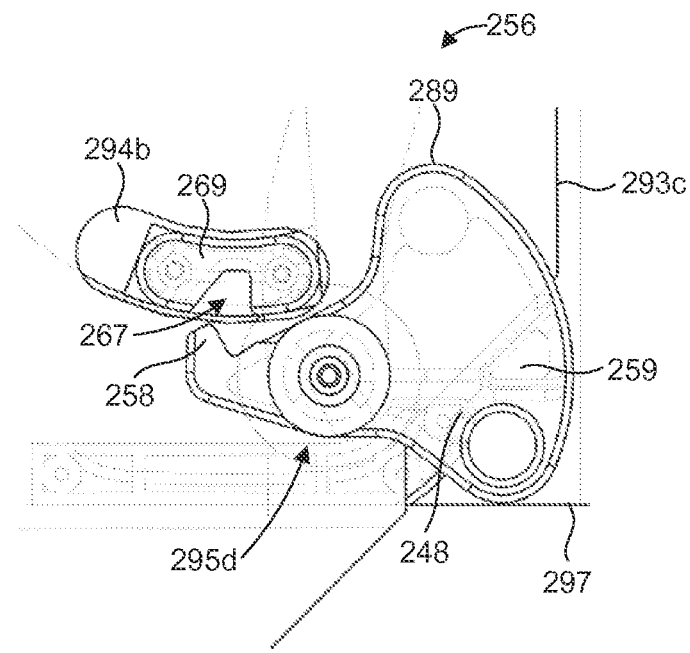
FIG. 18A illustrates a detail view of a linkage locking mechanism of the positioning device of FIG. 17 in an unlocked configuration in accordance with an example of the present disclosure.
Figure 18B:
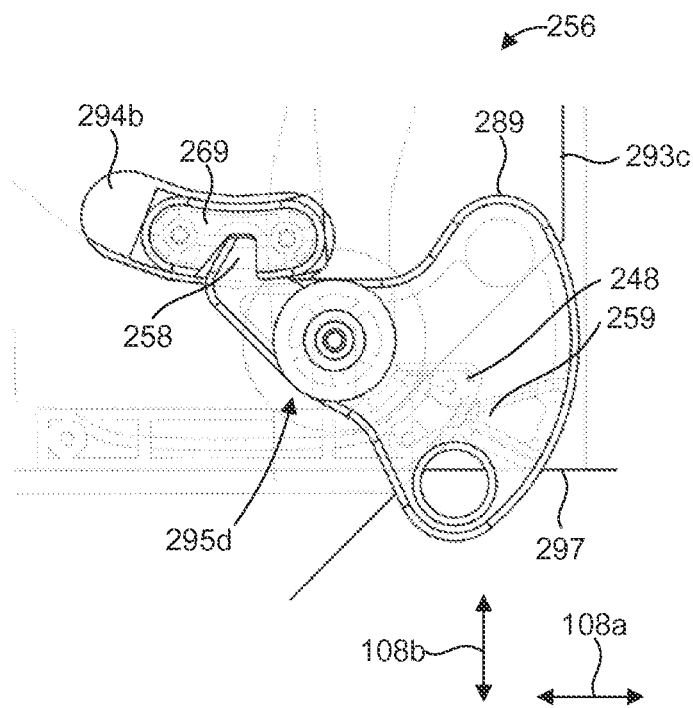
FIG. 18B illustrates a detail view of the linkage locking mechanism of the positioning device of FIG. 17 in a locked configuration in accordance with an example of the present disclosure.

FIGS. 18A and 18B illustrate a linkage locking mechanism 256 of the positioning device 290, in accordance with an example of the present disclosure. The linkage locking mechanism 256 is shown unlocked in FIG. 18A and locked in FIG. 18B. The linkage locking mechanism 256 can have a pivot member 289 rotatably coupled to a linkage member 293c of a first mechanism, such as at a pivot point 295d. The pivot member 289 can have a protrusion 258 configured to engage a notch 267 in a bracket 269 coupled to a linkage member 294b of a second mechanism. When thus engaged, the second mechanism is prevented from moving in direction or degree of freedom 108b. The pivot member 289, which is rotatably coupled to the linkage member 293c of a first mechanism, can also have a tab 259 configured to engage a portion of a bracket 248 that is coupled to a base 297. When thus engaged, the first mechanism is prevented from moving in direction or degree of freedom 108a. The linkage locking mechanism 256 can therefore simultaneously lock the first and second linkages from movement in directions 108a, 108b, which can be useful when transporting the positioning device 290.

Figure 19A:
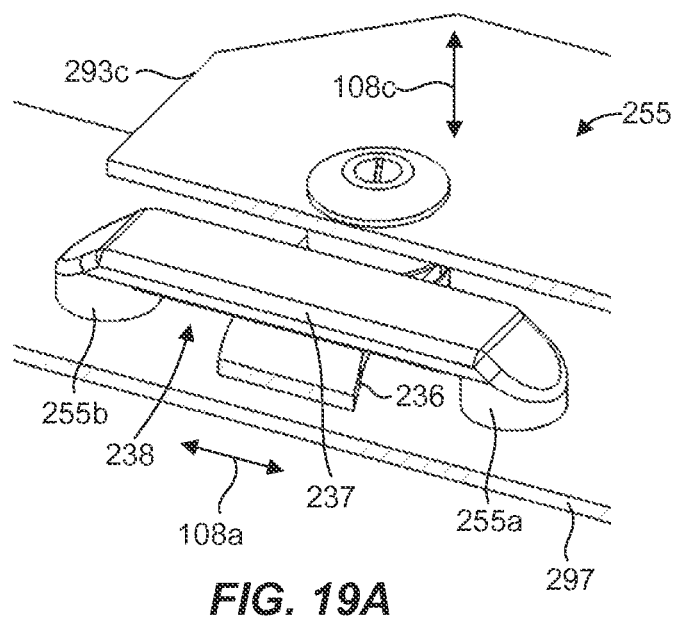
FIGS. 19A-19C illustrate features and components configured to limit movement of the positioning device of FIG. 17 in various directions.
Figure 19B:
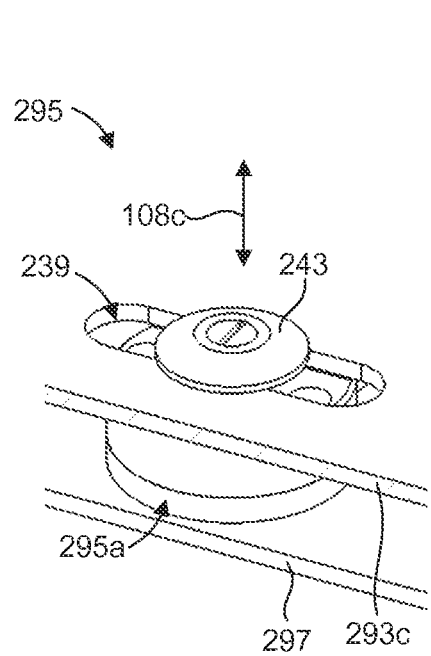
Figure 19C:
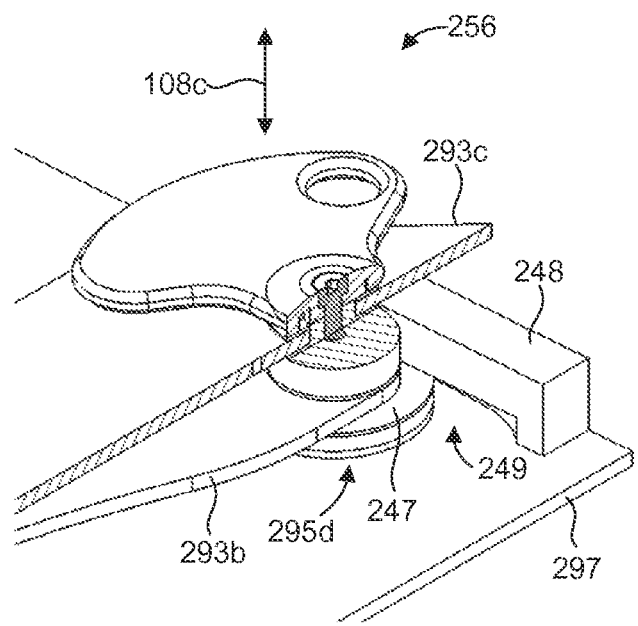

FIGS. 19A-19C illustrate features and components configured to limit movement of the positioning device in various directions. For example, a limit feature 255 (FIG. 19A) can serve as a range of motion limit stop for the positioning device 290. For example, the limit feature 255 can include range of motion limit stops 255a-b coupled to a base 297. A tab 236 can be coupled to the linkage member 293c of the first mechanism and can be configured to contact the range of motion limit stops 255a-b to limit the movement of the first mechanism in degree of freedom 108a. In addition, the limit feature 255 can include a span member 237 extending between the range of motion limit stops 255a-b and defining an opening 238 into which the tab 236 extends. The span member 237 can therefore provide a mechanical interference to movement of the tab 236, and therefore the linkage member 293c, and components coupled thereto, in a direction 108c. This can be useful when transporting the positioning device 290 and supporting the device by a handle 254. In this situation, flexibility of the linkage members can allow the various portions of the positioning device 290 to move or sag outward in direction 108c. The limit feature 255 can therefore be incorporated to prevent or minimize such movement.

A pivot point 295 (FIG. 19B) can be similarly adapted to limit or prevent undesirable movement in direction 108c. In this case, a portion of the pivot point structure 295a, which is coupled to the base 297, can extend through an opening 239 in the linkage member 293c. A flange 243 can extend over a portion of the linkage member 293c about the opening 239 to capture the linkage member 293c and prevent or limit movement of the linkage member 293c, and components coupled thereto, in direction 108c.

Likewise, structures associated with the linkage locking mechanism 256 can be adapted to limit or prevent undesirable movement in direction 108c. In this case, a portion (e.g., a flange 247) of the pivot point structure 295d, which is coupled to linkage members 293b, 293c, can extend at least partially into an opening 249 defined by the bracket 248 that is coupled to the base 297. The bracket 248 can extend over a portion of the flange 247 in the opening 249 to capture the linkage members 293b, 293c and prevent or limit movement of the linkage members, and components coupled thereto, in direction 108c. Components and structures of the positioning device 290 can thus be limited or prevented from undesirable movement in direction 108c at various locations.

Figure 20:
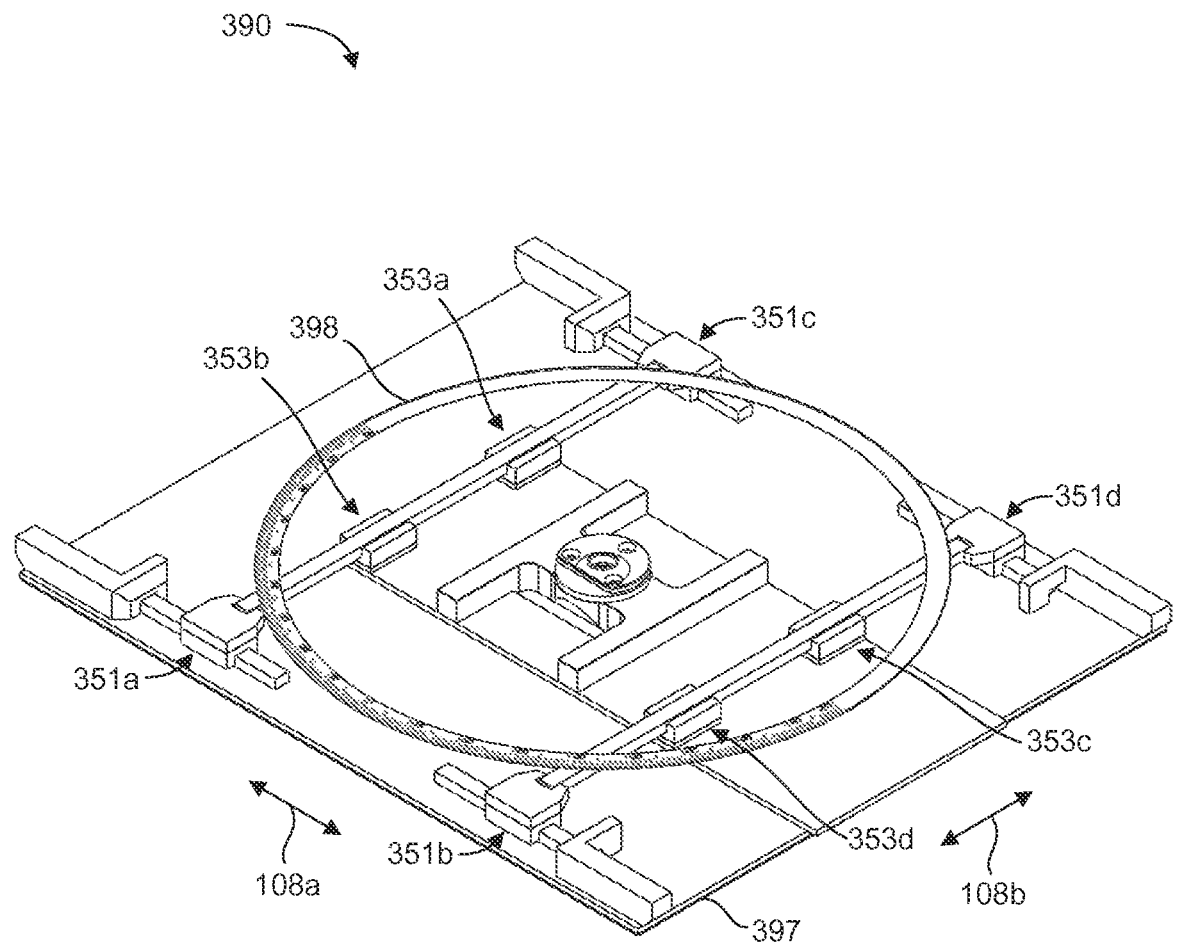
FIG. 20 illustrates a positioning device that can be included in a therapeutic ultrasound breast treatment system to movably adjust a position of an ultrasound breast treatment device, in accordance with yet another example of the present disclosure.

FIG. 20 illustrates a positioning device 390 that can be included in the therapeutic ultrasound breast treatment system 100 to movably adjust a position the ultrasound breast treatment device 101 relative to a patient, in accordance with yet another example of the present disclosure. The positioning device 390 can include a base 397 that supports linear bearings 351a-d for movement in translational degree of freedom 108a, which in turn support linear bearings 353a-d for movement in translational degree of freedom 108b. A rotatable member 398 can provide a rotational degree of freedom about a vertical axis.

It is to be understood that the above-referenced embodiments are illustrative of the application for the principles of the present invention. Numerous modifications and alternative arrangements can be devised without departing from the spirit and scope of the present invention while the present invention has been shown in the drawings and described above in connection with the exemplary embodiment(s) of the invention. It will be apparent to those of ordinary skill in the art that numerous modifications can be made without departing from the principles and concepts of the invention as set forth in the claims.

What is claimed is:

1. A therapeutic ultrasound breast treatment device, comprising:
   a receptacle to receive a breast of a patient therein;
   an ultrasound transducer assembly disposed proximate the receptacle and oriented to direct a high intensity ultrasound transmission to a focus location through an opening of the receptacle, said focus location within a target tissue region of the breast; and
   a flexible liner constructed of a flexible material disposed in the receptacle to contain an ultrasound coupling fluid about the breast, the liner having an extension portion that extends through the opening to form a seal with the ultrasound transducer assembly to prevent leakage of the ultrasound coupling fluid.

2. The device of claim 1, wherein the liner is optically transparent sufficient to visually inspect the breast through the liner.

3. The device of claim 1, wherein the liner comprises a flexible top to conform to the patient's anatomy around the breast.

4. The device of claim 1, wherein the liner is formed of silicone.

5. The device of claim 1, wherein the focus location of the ultrasound transmission is adjustable by moving the ultrasound transducer assembly, and wherein a portion of the liner extending through the opening is flexible to facilitate movement of the ultrasound transducer assembly.

6. The device of claim 1, wherein the focus location of the ultrasound transmission is adjustable by electronic steering.

7. The device of claim 1, wherein the liner is interchangeable with another liner of a different size to accommodate different sized breasts.

8. The device of claim 1, wherein the focus location of the ultrasound transmission is adjustable by moving the ultrasound transducer assembly.

9. The device of claim 1, further comprising: a radio frequency (RF) coil disposed within the receptacle proximate the breast or disposed about the transducer opening to facilitate monitoring treatment of the breast using magnetic resonance imaging (MRI).

10. The device of claim 9, wherein the RF coil is interchangeable with another RF coil of a different size to accommodate different sized breasts.

11. The device of claim 9, further comprising:
    a locking base adapted to couple to a floor of the receptacle; and
    at least one support member extending away from the locking base to orient the RF coil a predetermined height above the locking base, said RF coil being electrically coupled to the locking base.

12. The device of claim 1, further comprising:
    a radio frequency (RF) coil disposed about the transducer opening to facilitate monitoring treatment of the breast using magnetic resonance imaging (MM).

13. The device of claim 1, further comprising:
    a breast tensioning system to counteract buoyancy of the breast in the ultrasound coupling fluid, the breast tensioning system having a breast interface portion coupleable to the breast;
    a tensioning mechanism coupled to the breast interface portion to apply tension to the breast; and
    a tension line coupling the breast interface portion and the tension mechanism, the tension line extending through a base opening of the liner, wherein the liner separates the tensioning mechanism from the acoustic coupling fluid.

14. The device of claim 13, wherein the breast tensioning system comprises a locking mechanism to maintain tension on the breast.

15. The device of claim 13, wherein the breast tensioning system comprises a hand crank mechanically coupled to a gear train, said gear train connected to the breast interface portion via a tension line.

16. The device of claim 1, further comprising a plurality of tracking coils to determine the focus location of the ultrasound transmission to facilitate adjustment of the focus location.

17. A positioning device to movably adjust a position of the therapeutic ultrasound breast treatment device of claim 1 relative to a patient, comprising:
    a base;
    a first linkage coupled to the base, the first linkage being configured to provide
       straight line motion or quasi-straight line motion for at least a first portion of the first linkage within a range of motion of the first linkage in
       a first translational degree of freedom; and
    a second linkage coupled to the first portion of the first linkage, the second linkage being configured to provide straight line motion or quasi-straight line motion for at least a second portion of the second linkage within a range of motion of the second linkage in a second translational degree of freedom,
    wherein the second portion of the second linkage is positionable in the first translational degree of freedom by motion of the first linkage, and
    wherein the second portion of the second linkage is positionable in the second translational degree of freedom by motion of the second linkage.

18. The positioning device of claim 17, wherein at least one of the first linkage and the second linkage comprises a Watt linkage, a Peaucellier-Lipkin linkage, Hart linkage, a Chebyshev linkage, a Hoekens linkage, a Sarrus linkage, a Scott Russell linkage, or a combination thereof.

19. The positioning device of claim 17, further comprising a rotatable member rotatably coupled to the second portion of the second linkage to provide a rotational degree of freedom.

20. The positioning device of claim 17, further comprising a third linkage coupled to the first linkage and the second linkage.

* * * * *